US009868650B2

(12) United States Patent
Allen et al.

(10) Patent No.: US 9,868,650 B2
(45) Date of Patent: Jan. 16, 2018

(54) METHOD FOR REMOVING GLYPHOSATE FROM A SOLUTION USING FUNCTIONALIZED POLYMERIC NANOPARTICLES

(71) Applicant: International Business Machines Corporation, Armonk, NY (US)

(72) Inventors: Robert D. Allen, San Jose, CA (US); Geraud J. Dubois, Los Altos, CA (US); Young-Hye Na, San Jose, CA (US); Lianna C. Samuel, Santa Clara, CA (US); Joseph Sly, San Jose, CA (US); Ran Wang, Sunnyvale, CA (US)

(73) Assignee: International Business Machines Corporation, Armonk, NY (US)

( * ) Notice: Subject to any disclaimer, the term of this patent is extended or adjusted under 35 U.S.C. 154(b) by 199 days.

(21) Appl. No.: 14/977,571

(22) Filed: Dec. 21, 2015

(65) Prior Publication Data
US 2017/0174535 A1   Jun. 22, 2017

(51) Int. Cl.
| C02F 1/42 | (2006.01) |
| C02F 1/28 | (2006.01) |
| B01D 61/00 | (2006.01) |
| B01D 1/28 | (2006.01) |
| B01J 49/00 | (2017.01) |
| B01D 15/04 | (2006.01) |
| C07F 9/38 | (2006.01) |
| B01D 15/26 | (2006.01) |
| C02F 101/30 | (2006.01) |
| C02F 101/34 | (2006.01) |

(52) U.S. Cl.
CPC ............ *C02F 1/285* (2013.01); *B01D 15/265* (2013.01); *C07F 9/3808* (2013.01); *C02F 2101/306* (2013.01); *C02F 2101/34* (2013.01)

(58) Field of Classification Search
None
See application file for complete search history.

(56) References Cited

U.S. PATENT DOCUMENTS

| 5,898,082 A | 4/1999 | Hodgkinson | |
| 6,127,481 A * | 10/2000 | Janssen | C08F 290/04 525/106 |
| 7,750,180 B2 | 7/2010 | Coleman et al. | |
| 8,669,396 B2 | 3/2014 | Choi et al. | |
| 8,765,098 B2 * | 7/2014 | Appel | A61K 47/48176 424/400 |
| 2003/0042201 A1* | 3/2003 | Sizelove | A61K 35/02 210/639 |
| 2011/0243848 A1* | 10/2011 | Appel | A61K 47/48176 424/9.1 |

(Continued)

OTHER PUBLICATIONS

Speth, "Glyphosate Removal From Drinking Water," Journal of Environmental Enginerring, vol. 119, No. 6, Nov./Dec. 1993, pp. 1139-1157.

(Continued)

*Primary Examiner* — Ana Fortuna
(74) *Attorney, Agent, or Firm* — Shumaker & Sieffert, P.A.

(57) ABSTRACT

A method for removing glyphosate from a solution by contacting the solution with a polymeric particle including a moiety selected from the group consisting of ammonium, amine and combinations thereof, wherein the moiety is positively charged in the solution.

14 Claims, 6 Drawing Sheets

(56) References Cited

U.S. PATENT DOCUMENTS

| | | | |
|---|---|---|---|
| 2011/0303871 A1* | 12/2011 | Burba | C02F 1/288 |
| | | | 252/184 |
| 2012/0261611 A1* | 10/2012 | Hassler | C02F 1/5236 |
| | | | 252/182.3 |
| 2014/0370064 A1* | 12/2014 | Lee | A01N 25/34 |
| | | | 424/405 |
| 2017/0174535 A1* | 6/2017 | Allen | C02F 1/285 |

OTHER PUBLICATIONS

Milojevic-Rakic et al., "Polyaniline and its composites with zeolite ZSM-5 for efficient removal of glyphosate form aqueous solution," Journal of Microporous and Mesoporous Materials, vol. 180, Nov. 1, 2013, pp. 141-155.

* cited by examiner

METHOD FOR REMOVING GLYPHOSATE FROM A SOLUTION USING FUNCTIONALIZED POLYMERIC NANOPARTICLES

BACKGROUND

Glyphosate, a type of organophosphate with the molecular structure shown below, has been widely used as a herbicide, and subsequently has entered into waterways and the drinking water supply:

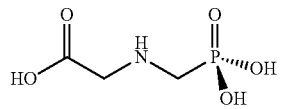

However, even at an ultra-dilute concentrations (about 1 part per million (ppm) to about 1 part per billion (ppb)), glyphosate has been found to damage the environment. Since glyphosate has a low molecular weight, high solubility in water, and a relatively long half-life, removing ultra-dilute glyphosate from water can be challenging using conventional filtration techniques.

For example, current approaches for removing glyphosates include chlorination, ozonation, membrane filtration, UV irradiation and adsorption onto various materials, which can be employed either separately or in combination. However, these removal techniques are slow and can be relatively expensive.

UV irradiation and ozonation break down glyphosate to small molecules, and the extent to which this degradation is complete depends on both the length of contact time and initial concentration of the glyphosate. Incomplete molecular degradation from UV irradiation and ozonation can form smaller molecules (e.g., aminomethyl phosphonic acid), which can potentially be more damaging to the environment than glyphosate. Thus, to ensure full removal of the glyphosate and its byproducts, the contact time of the contaminated water and the UV or ozonation system should be on the order of hours, which makes these processes unacceptable for commercial processes with short production times.

Activated carbon is another frequently used method for water purification that can be ineffective in reliably removing glyphosate from a solution such as water. While humic acids, clays and other natural materials can also be used for glyphosate removal, high salt concentrations in the water can reduce their efficiency. Humic acids, clays and other natural materials can also foul membranes used in purification processes.

SUMMARY

The present disclosure is directed to a method for quickly and effectively removing glyphosate from a solution with functionalized nano-scale block copolymers. In some embodiments, the copolymers include a hydrophobic polymeric core and polymeric arms having thereon positively charged functional groups such as, for example, ammonium or amine. The method of the present disclosure is fast, easy to scale up, and can adsorb glyphosate without affecting other solutes in the solution.

In some embodiments, the functionalized block copolymers described in this disclosure can remove more than 94% of glyphosate from an aqueous solution, compared with about 32% removal by activated carbon, a commonly used adsorbent material. In some embodiments, the functionalized block copolymers of this disclosure also have a much faster glyphosate removal rate and a higher removal capacity from aqueous solution compared to activated carbon.

In one aspect, the present disclosure is directed to a method for removing glyphosate from a solution by contacting the solution with a polymeric particle including a moiety selected from the group consisting of ammonium, amine and combinations thereof, wherein the moiety is positively charged in the solution.

In another aspect, the present disclosure is directed to a method for removing glyphosate from an aqueous solution, including: (a) adding an amine-functionalized polymeric particle into the aqueous solution containing glyphosate; and (b) filtering to remove from the aqueous solution a complex including the amine-functionalized polymeric particles with glyphosate adsorbed thereon, and residual amine-functionalized particles.

In another aspect, the present disclosure is directed to a filtration column including a packing including a polymeric particle with the following chemical structure:

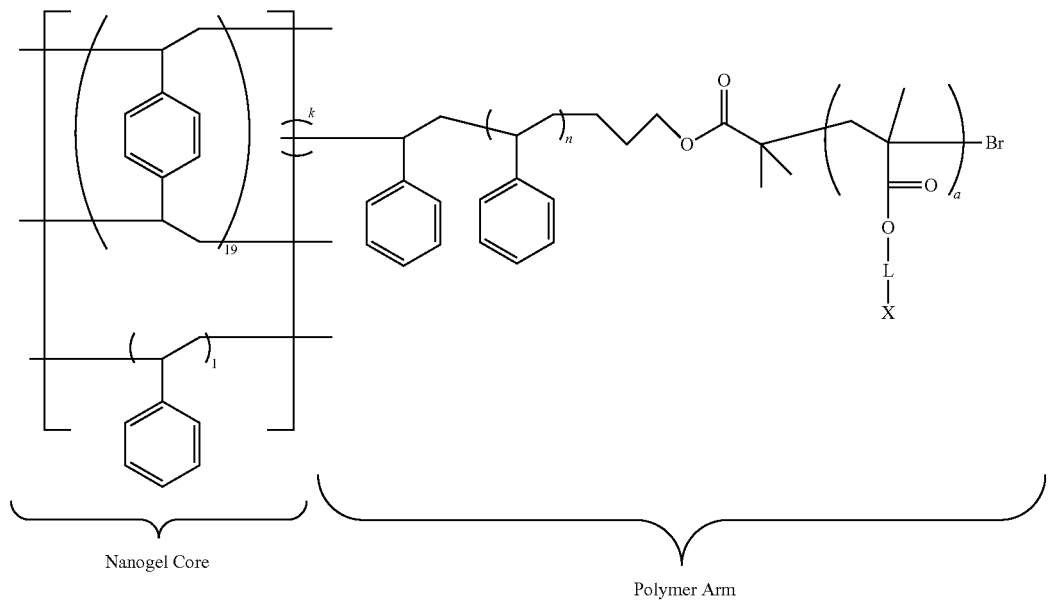

wherein the linking group (L) is selected from the group consisting of alkyl, aryl, alkenyl and combinations thereof; X is selected from the group consisting of positively charged ammonium moieties and their precursors; k is 6 or more, n is 1 or more, and a is 2 or more; and an aqueous solution contacting the packing, wherein the aqueous solution includes less than about 5 ppm glyphosate.

In another aspect, the present disclosure is directed to a filter including a polymeric particle with the following chemical structure:

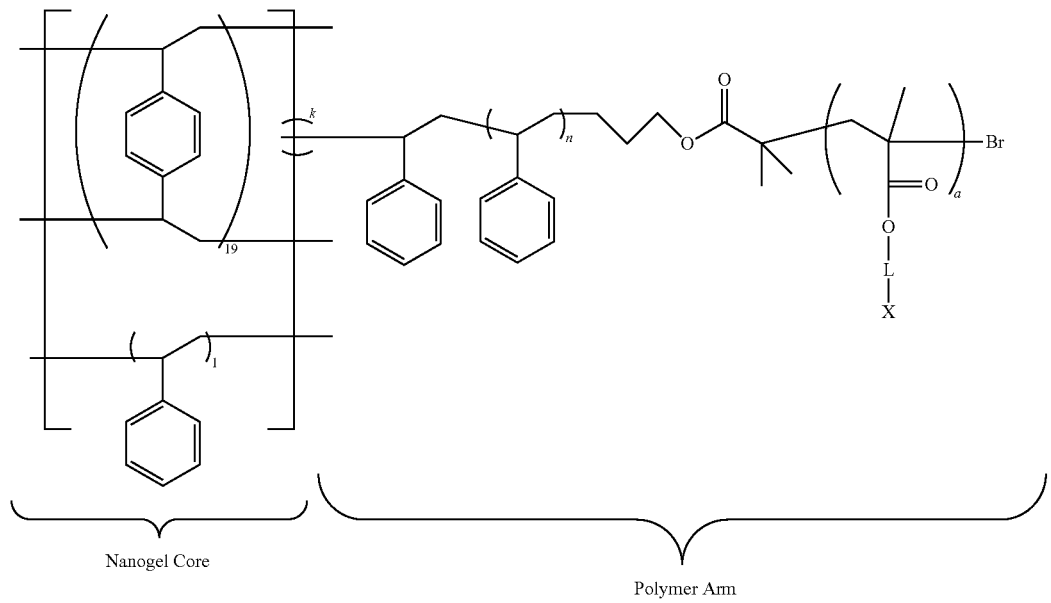

wherein the linking group (L) is selected from the group consisting of alkyl, aryl, alkenyl and combinations thereof; X is selected from the group consisting of positively charged ammonium moieties and their precursors; k is 6 or more, n is 1 or more, and a is 2 or more; and an aqueous solution contacting the filter, wherein the aqueous solution includes less than about 5 ppm glyphosate.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the figures indicate like elements.

DETAILED DESCRIPTION

Figure 1:
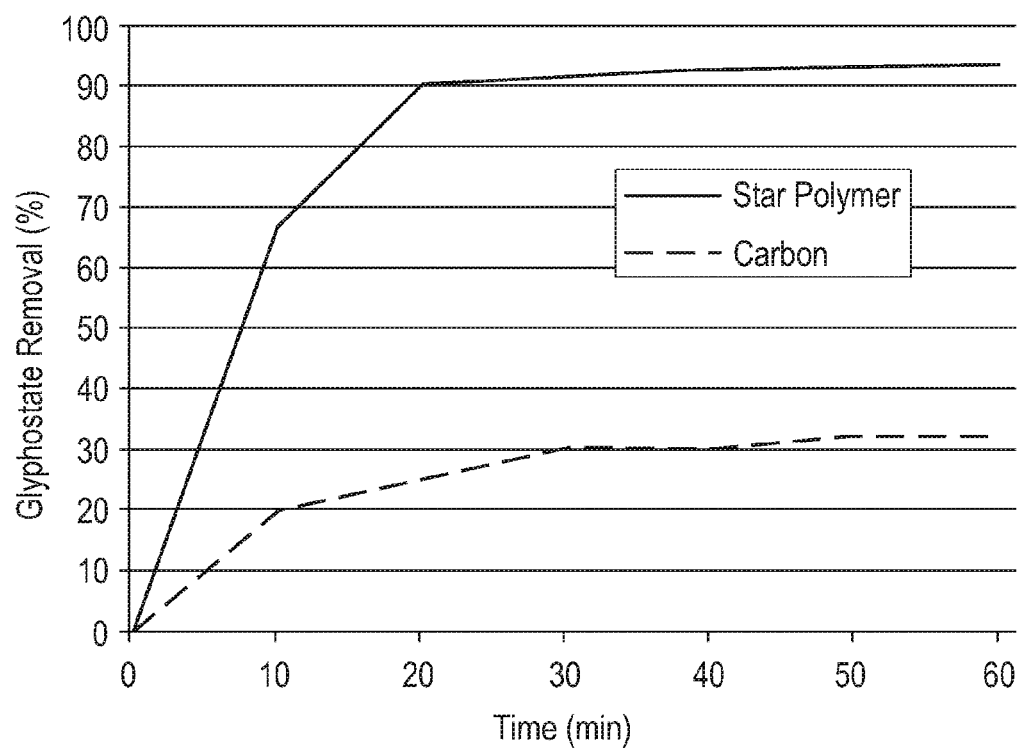
FIG. 1 is a plot of glyphosate (5 ppm) removal vs. time by a star-shaped block copolymer and activated carbon.

The present disclosure is directed to a method for quick and efficient removal of glyphosate from an aqueous solution by contacting the aqueous solution with a filtration medium including a nano-scale block copolymer functionalized with a positively charged moiety such as, for example, ammonium, amine and combinations thereof.

In some embodiments, the nano-scale block copolymers in the filtration medium include star polymers with a central core and a plurality of positively functionalized arms on, and extending outward from, the core. In various embodiments, the central core could be hydrophilic or hydrophobic, and is preferably hydrophobic to enhance durability of the star polymers when exposed to an aqueous solution. In this disclosure the term "star polymer" refers to any branched polymer or copolymer including a plurality of linear polymer arms (at least six) attached at a central core. The Matyjaszewski group at Carnegie Mellon University provides general information regarding the structure and synthesis of various star copolymers at a site given by the concatenation of "cmu.edu" and "maty/materials/Polymers_with_specific_Architecture/star-copolymers.html."

The central core of the star polymers can be an atom, molecule, or macromolecule, or a globular nanogel (i.e., a cross-linked polymer gel of nanoscale proportions), and in some embodiments the core itself may be multifunctional. In various embodiments, the core contains aromatic, aliphatic, or mixed substituents with carbon only or mixtures containing heteroatoms. In some embodiments, the core is cross-linked and contains a plethora of surface functionality. In some embodiments, the core retains its shape by covalent crosslinking, although it could also be held together by electrostatic, hydrogen bonding, pi-stacking, or metal-ligand interactions.

In various embodiments, the core of the star polymers includes a hydrophobic polymer, and suitable examples include, but are not limited to, polyolefins, polystyrene (PS), poly(alkylmethacrylate), polyacrylamide, polycarbonate and polyester.

The "arms" of the star polymers include variable-length organic chains, which can be made of similar or different monomers. The arms can be chemically identical (homostars) or different (heterostars or miktoarm stars). In other embodiments, the arms may include multiple monomers or polymers, resulting in star-block polymers or random star copolymers. In various embodiments, the star polymers include at least 6, or at least 10, or at least 20, or at least 30, or at least 60, arms covalently attached to the core.

In various embodiments, the hydrophilic arms include positively charged ammonium moieties and/or their precursors (for example, amines). In various embodiments, the functionalized arms of the star polymers include (meth)acryl functionality, wherein (meth)acryl includes acrylates and methacrylates. Suitable (meth)acryl functional groups for the star polymer arms include, but are not limited to, amino-functional (meth)acrylates such as dimethylaminoethyl methacrylate (DMAEMA).

In some embodiments, which are not intended to be limiting, the amine-functionalized star shaped polymeric particle has a particle size of about 10 nm to about 500 nm, or about 20 nm to about 200 nm, and a zeta potential of about 5 mV to about 50 mV, or about 10 mV to about 25 mV.

In one non-limiting embodiment, a suitable star polymer for the filtration medium is a star-shaped block copolymer with a crosslinked polystyrene core and functionalized arms having thereon moieties that are positively charged under substantially neutral pH conditions. An example is shown in Formula I below:

units and an arrangement of 6 or more, 10 or more, 20 or more, 30 or more, or 60 or more, polymeric arms attached to the nanogel core.

As noted in Formula I, a linking portion L of the polymeric arms attached to the nanogel core is formed from n units of homopolymers or random copolymers with monomeric units including alkyl, cycloalkyl, alkoxy, ether, aryl and combinations thereof, wherein n is greater than about 1, or about 10, or about 20, or about 50, or about 60.

As set forth in Formula I, the star polymer includes a positively charged moiety X attached to the linking group L, and suitable examples of the positively charged moiety X include, but are not limited to, ammonium, amines and combinations thereof. In some embodiments, the positively charged moiety X can be a primary amine, a secondary amine, a tertiary amine, or combinations thereof. The positively charged moiety X can be on the terminal surface or anywhere along the arms of the star polymer.

For example, in some embodiments the star-shaped block copolymer can include a polystyrene core and methacrylate polymer arms functionalized with an amines such as, for example, a tertiary amine such as $N(CH_3)_2$. In some non-limiting embodiments, the positively charged functional region of the star polymer of Formula I can include dimethylaminoethyl (meth)acrylate (DMAEMA) containing monomers. The amine-functionalized species such as DMAEMA form positively-charged ammonium species under neutral pH conditions or in the presence of acidic compounds, and as such can be highly effective in bonding with dilute levels of glyphosate in aqueous solutions.

Formula I

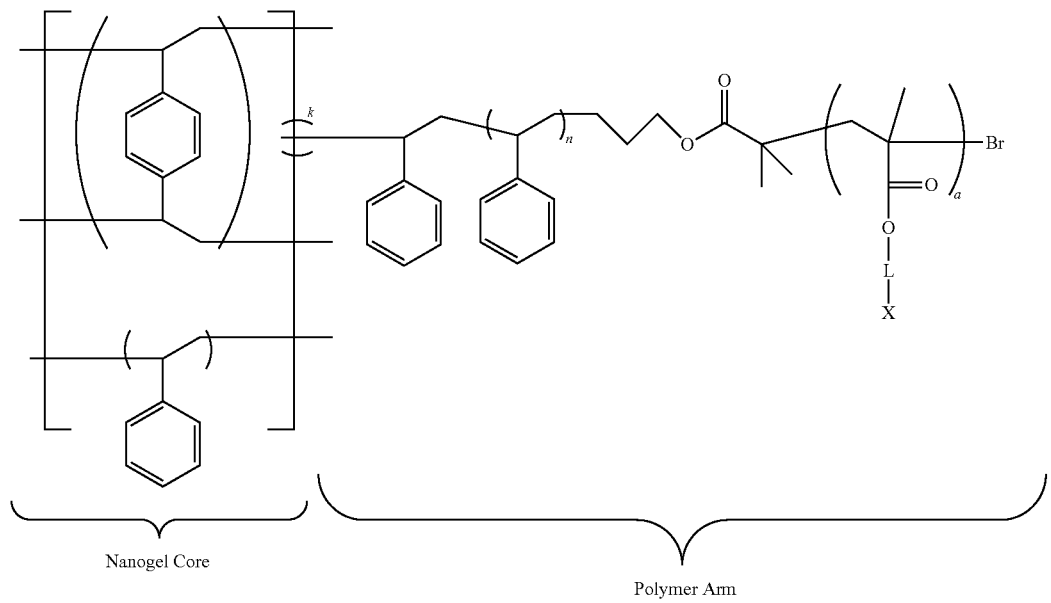

Nanogel Core

Polymer Arm

In Formula I, k is greater than or equal to about 6, n is greater than about 1, and a is 2 or more. In Formula I, the star polymer includes a hydrophobic polymeric globular nanogel polystyrene (PS) core with aromatic monomeric In one embodiment, which is not intended to be limiting, the star polymer has the structure shown in Formula II below, wherein a is about 33, n is about 32, k is about 35, and Me=methyl ($CH_3$):

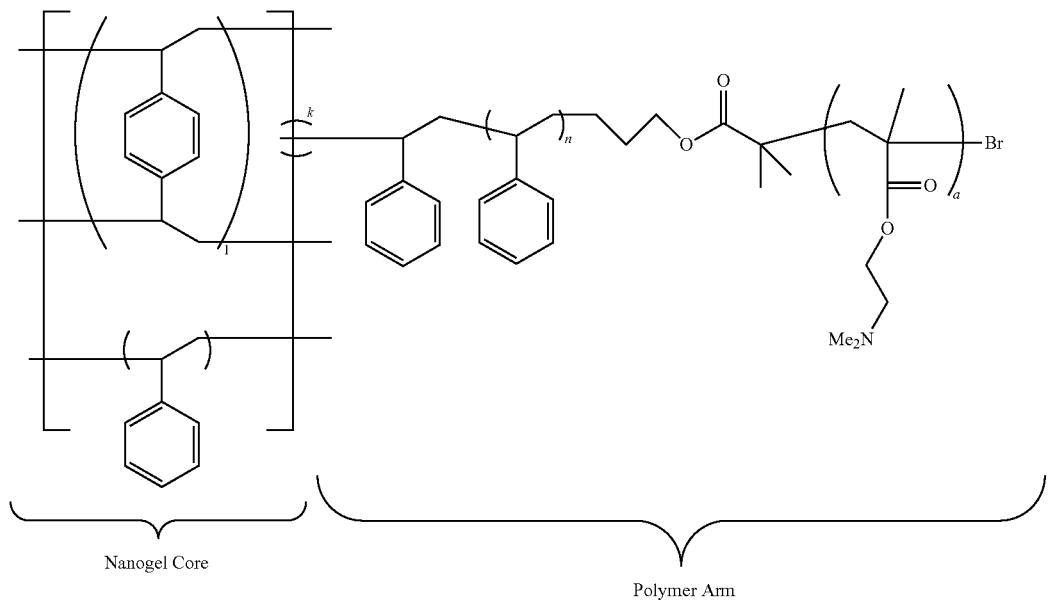

Formula II

Nanogel Core | Polymer Arm

Star-shaped polymers can be synthesized through various approaches. The most common syntheses include an arm-first approach, in which the living chains are used as the initiators, and a core-first approach, in which the core is used as the initiator. Other synthetic routes include: controlled sol-gel processes, group transfer polymerization, transition metal catalysis, living anionic polymerization, living cationic polymerization, ring opening polymerization, ring-opening metathesis polymerization (ROMP), atom transfer radical polymerization (ATRP), reversible addition-fragmentation chain transfer polymerization (RAFT) and nitroxide mediated radical polymerization.

A wide variety of glyphosate-containing solutions can be processed by a filtration medium including the star polymer materials described herein. In various embodiments, the solutions can have dilute concentrations of glyphosate such as, for example, from about 5 parts per billion (ppb) to 1000 parts per million (ppm). In various embodiments, the solutions can include any aqueous or organic solvent, or combinations thereof, that can dissolve glyphosates, although aqueous solutions are preferred. In various embodiments, the solution can have a wide range of pH values from about 1 to about 11, or about 3 to about 10.

As a non-limiting example, in processing environments where the pH of the aqueous solution contacting the inorganic mesoporous material is substantially neutral (a pH of about 6 to about 8, or a pH of about 7), the first phosphonic proton and the carboxylate proton from glyphosate are fully dissociated, so the star-shaped block copolymer can efficiently adsorb the deprotonated glyphosate in a short period of time by charge interaction with its extremely high surface area and the large number of amine groups on the polymer arms.

The star polymer filtration material can be contacted with the solution in a wide variety of ways such as, for example, allowing the solution to migrate through a layer of packing in a column including a granular bed incorporating the star polymer material. In such a column, the packing can optionally include other fillers such as, for example, non-functionalized inorganic particles, diatomaceous earth, cellulose, perlite, and the like.

In another embodiment, the star polymer material is incorporated in a filter construction to adsorb glyphosate as the glyphosate-containing solution moves through the filter.

In another embodiment, the glyphosate-containing solution is stirred together with the star polymer material for a time sufficient to ensure contact between the glyphosate and the positively charged functional groups on the star shaped block copolymers. In various embodiments, which are not intended to be limiting, the stirring time can be about 1 minute to about 1 hour. A complex including the star polymer material and adsorbed glyphosate, as well as residual star polymer material, can subsequently be removed by an additional filtration step such as, for example, sand filtration, microfiltration, ultrafiltration, and combinations thereof.

The pressure or temperature for the solution can vary widely depending on the type of filter used in the process. For example, the operational pressure using ultrafiltration is about 30 to about 70 pounds per square inch (psi), and microfiltration is typically less than about 30 psi. Operational temperature can vary depending on the stability of functional groups on the arms of the star polymers. For example, mild heat conditions (greater than about 20° C. and less than about 50° C.), or room temperature, are preferred.

Embodiments of the invention will now be described with reference to the following non-limiting examples.

EXAMPLES

Materials

Functional polymeric particles referred to herein as star-shaped block copolymers were synthesized as described in, for example, U.S. Patent Publication No. 20110243848 A1. The ratio of the arm composition in the block copolymers was easily controlled during synthesis.

Particle size and surface charge density of the star-shaped block copolymer solution (0.1 wt %) were measured by dynamic light scattering (DLS), using a Malvern Zetasizer Nano-ZS (Malvern Instruments Ltd., Worcestershire, UK). Three series of 11 measurements were performed, and the average particle size was calculated with a known size of polystyrene latex standard. The zeta potential was calculated from electrophoretic mobility measurements in three series of 20 measurements, and the measurement temperature was set at 25° C.

The adsorbate used in this experiment was analytical grade glyphosate obtained from Sigma-Aldrich, Wisconsin, USA, under the trade designation Pestanal. 0.01 grams of glyphosate was dissolved in 1 liter of deionized water, to create a stock solution (~10 ppm). All other initial concentrations utilized herein were made by diluting the stock solution with deionized water.

The other adsorbents tested were activated carbon and the dendritic polyamidoamine (PAMAM) 6, also purchased from Sigma-Aldrich.

General Procedure for Solution Preparation and Characterization

Glyphosate solution with an initial concentration of 5 ppm was used to determine the adsorption efficiency of the adsorbents. The vials were sealed and the mixtures stirred for predetermined time intervals, up to 1.5 hours.

After each time interval, the mixture was filtered to remove the adsorbents and any captured glyphosate. The concentration of glyphosate was then measured using inductively coupled plasma spectrometer available from Thermo Scientific under the trade designation ICAP 6300 Duo View Spectrometer, which has a solid stated CID detector and a detection limit of 2 ppb for phosphorous (P) in deionized water. The amount of adsorption, $q_t$ (mg/g) at each time was determined by:

$$q_t = (C_0 - C_t)V/W$$

where $C_0$ is the initial concentration of glyphosate, $C_t$ is the glyphosate concentration after time, t, V is the volume of solution and W is the weight of adsorbent used. Final adsorption efficiencies were used to determine which adsorbent is most effective in removing glyphosate.

Example 1

Glyphosate Removal Test by Functional Polymeric Particle

A glyphosate solution with initial concentration of 5 ppm was used to determine the adsorption efficiency of the functional star-shaped block copolymers. The particle size of the star-shaped block copolymer was ~56 nm and its chemical potential was about +28 mV.

Example 2

Glyphosate Removal Test by Activated Carbon

The glyphosate solution with initial concentration of 5 ppm was used to determine the adsorption efficiency of the activated carbon. Activated carbon has a large surface area and a low price, and is considered as one of the most widely used adsorbents. However, the negative surface charge (−20 mV) limits its application on glyphosate removal. As shown in FIG. 1, the removal rate is only 32%.

Example 3

Glyphosate Removal Test by Dendrimer (PAMAM 6)

The glyphosate solution with initial concentration of 5 ppm was used to determine the adsorption efficiency of the dendrimer (PAMAM 6). PAMAM 6 has a high surface area and primary amine groups on the terminal surface. Compared with the functional star-shaped block copolymer, PAMAM 6 has a relatively low density of amine groups. The consequence is shown in FIG. 2, as the limited amine groups on the terminal surface of PAMAM 6 are insufficient for effective removal of glyphosate.

Figure 2:
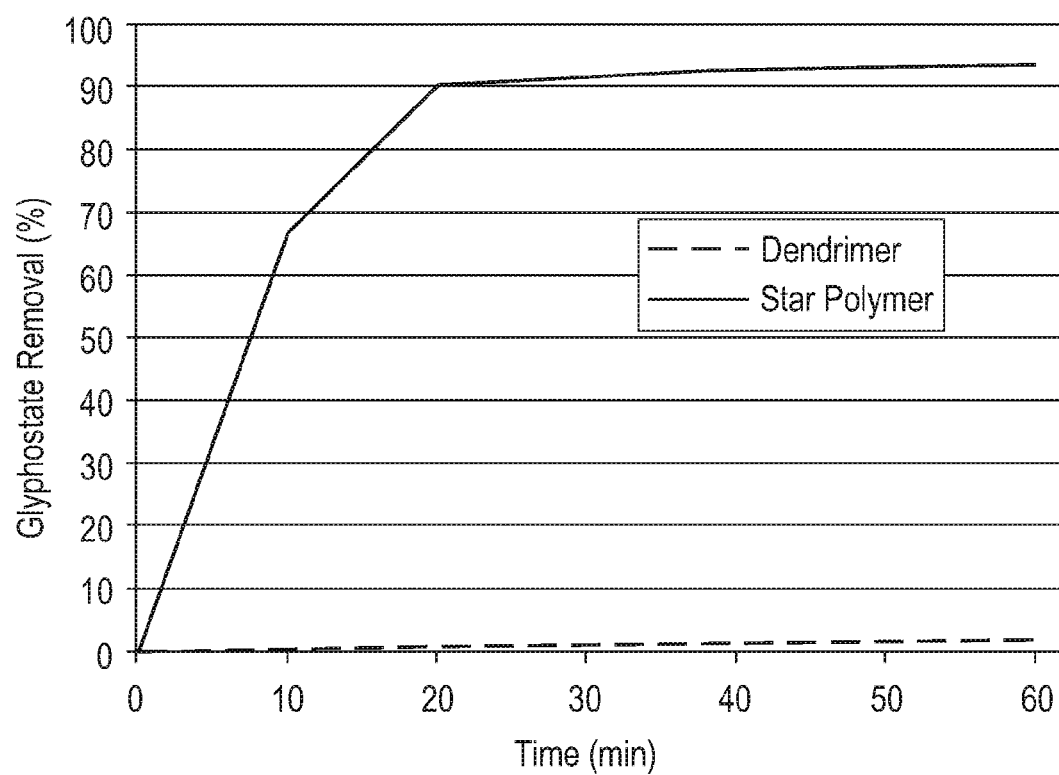
FIG. 2 is a plot of glyphosate (5 ppm) removal vs. time by a star-shaped block copolymer and the dendrimer PAMAM 6.

As shown in FIGS. 1-2, the star-shaped block copolymer showed an outstanding glyphosate removal rate. About 94% glyphosate in the ultra-dilute solution (5 ppm) was successfully removed. The removal rate is much higher than those of the activated carbon (32%) (FIG. 1) and the dendrimer PAMAM 6 (less than 10%) (FIG. 2).

While not wishing to be bound by any theory, presently available evidence indicates that this removal efficiency can be attributed to the high surface area of the star polymer particles, and also the high density of the amine groups on the terminal surface and along the arms of the star polymer particles.

Example 4: Kinetic Study of Glyphosate Removal

A glyphosate solution with an initial concentration of 5 ppm was used to study the kinetics of glyphosate removal by a star shaped block copolymer. Glyphosate removal by activated carbon was also performed as a benchmark.

The adsorption kinetics associated with the glyphosate removal for each adsorbent were compared to the Lagergren and pseudo-second order kinetic equations. The first equation used to describe the adsorption of an adsorbate from aqueous solution is Lagergren's kinetic equation. This equation assumes that the adsorption of the adsorbate onto the adsorbent at a rate given by:

$$dq_t/dt = k_1(q_e - q_t)$$

where $q_e$ and $q_t$ are the adsorption capacities at equilibrium and at time t, respectively and $k_1$ is the rate constant of a pseudo-first order adsorption process. Given that at time t=0 $q_t$=0, and at time t=t $q_t$=$q_t$, the above equation can be integrated between the boundaries of t=0 and t=t, to give the following equation:

$$q_t = q_e(1 - e^{-kt})$$

which can be linearized into the Legergren equation:

$$\log(q_e - q_t) = \log(q_m) - k_1 t/2.303$$

Thus the rate constant can be determined by plotting vs t.

In pseudo-second order adsorption kinetics, we assumed that the adsorbate gets adsorbed onto two surface sites and is represented by the equation:

$$dq_t/dt = k_2(q_e - q_t)^2$$

where $k_2$ is the rate of second-order adsorption (g/mg min). This equation can be separated, and then integrating to the same limits as before, gives:

$$1/(q_e - q_t) = 1/q_e + k_2 t$$

While this equation can be linearized into five different forms, the most widely accepted form was used in this study:

$$t/q_t = 1/(k_2 q_e^2) + t/q_e$$

From this equation $k_2$ can be found from plotting $t/q_t$ vs t.

The adsorption kinetics may be described by a simple first order reaction, in which the reaction rate depends on the concentration of only one reactant, or a pseudo second order equation, in which the reaction rate mainly depends on the concentration of two reactants.

The adsorption kinetics may be described by a simple first order reaction, in which the reaction rate depends on the concentration of only one reactant. In the alternative, the adsorption kinetics may follow a pseudo second order equation, in which the reaction rate mainly depends on the concentration of two reactants.

Figure 3A:
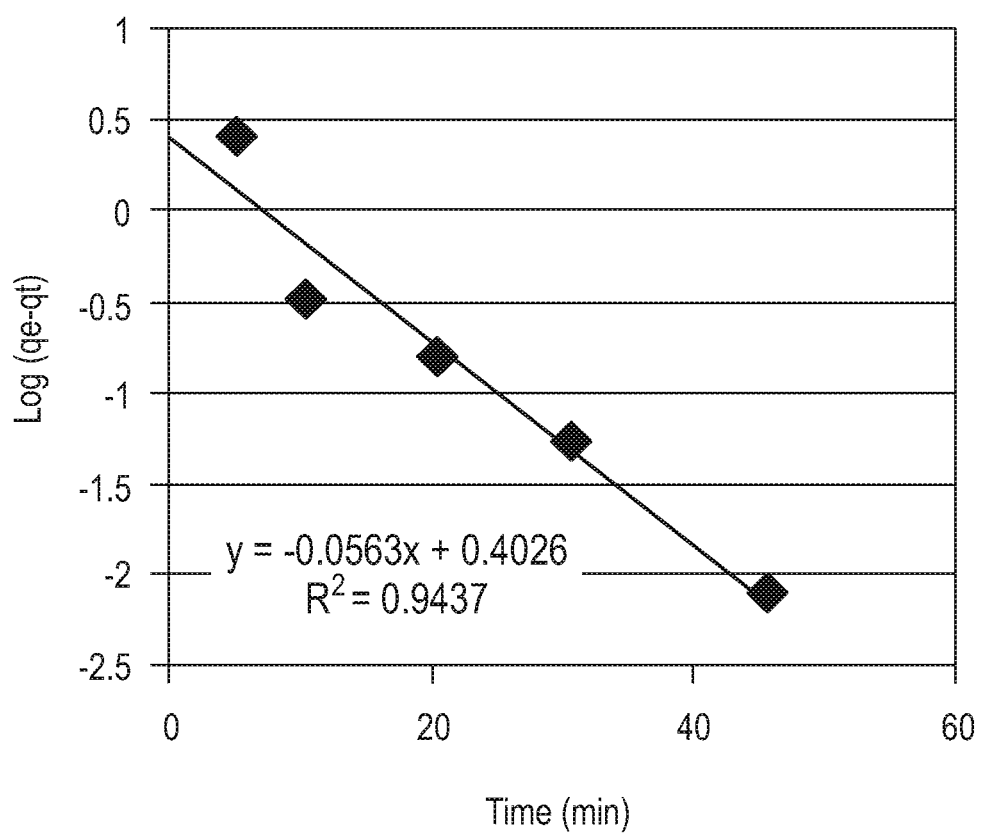
FIG. 3A is a plot of a kinetic study of glyphosate removal by a star shaped block copolymer with a first-order model.
Figure 3B:
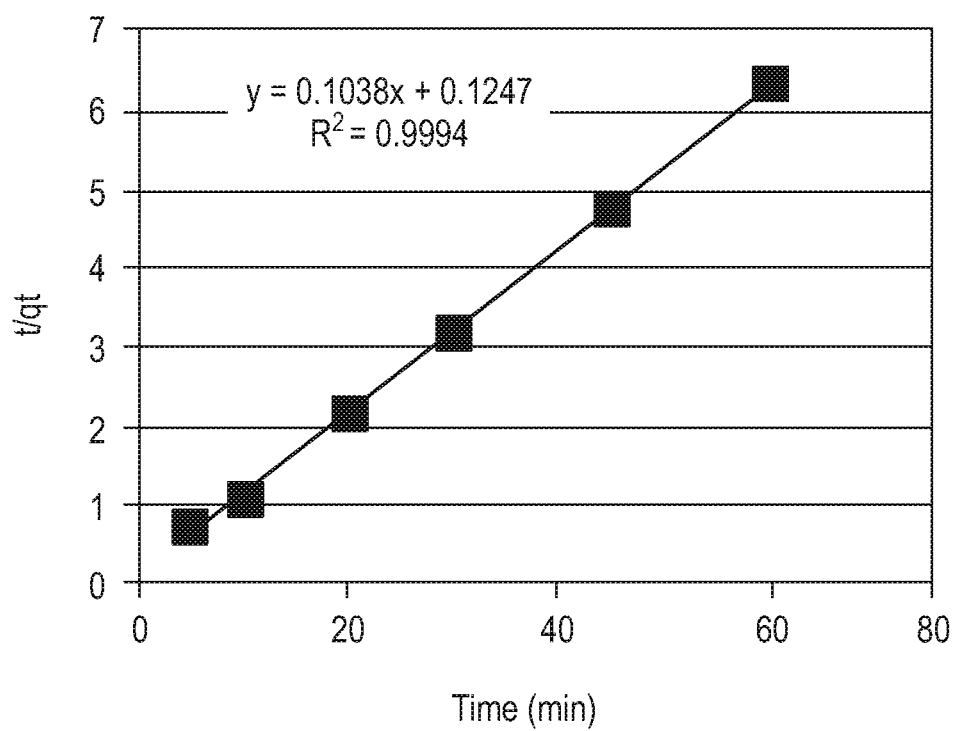
FIG. 3B is a plot of a kinetic study of glyphosate removal by a star shaped block copolymer with a second-order model.

As indicated in FIG. 3A, the simulated correlation factor based on first order adsorption by the star polymer is only 0.9437, far from a good correlation. On the contrary, as shown in FIG. 3B, the second order modeling gave a very good fit with a good correlation factor of 0.9994. So, these data show that glyphosate removal by a functionalized star polymer better fits the second order adsorption model.

Figure 4A:
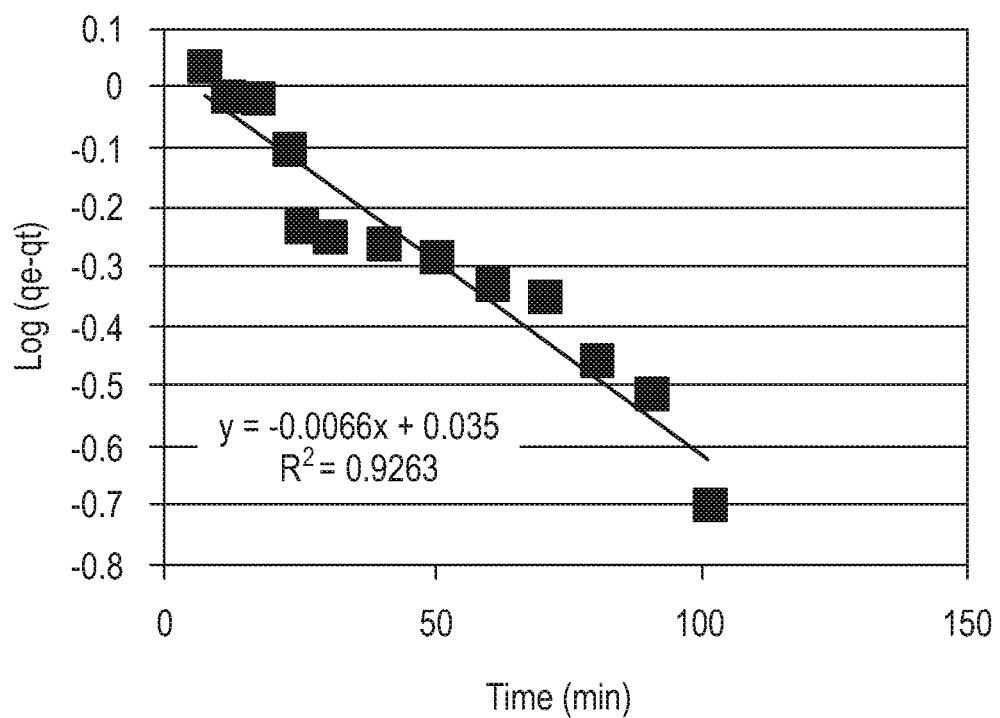
FIG. 4A is a plot of a kinetic study of glyphosate removal by activated carbon (AC) with a first-order model.
Figure 4B:
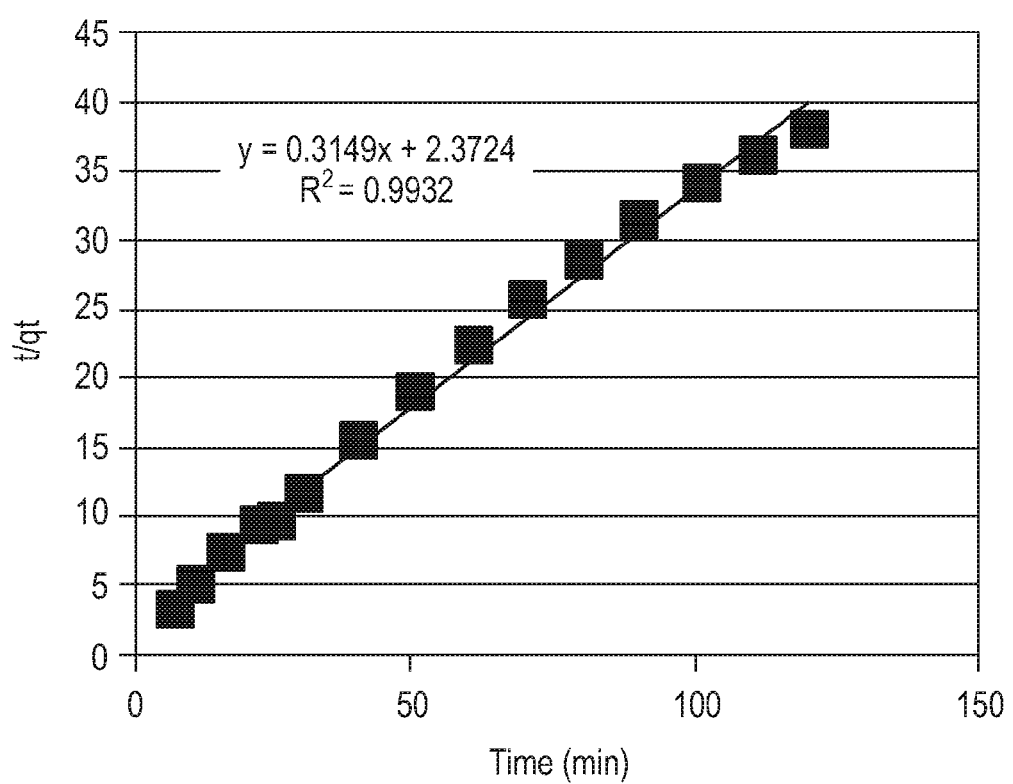
FIG. 4B is a plot of a kinetic study of glyphosate removal by AC with a second-order model.

Glyphosate removal by activated carbon (AC) also fits better in a second-order reaction (FIG. 4B) than a first order reaction (FIG. 4A) (R-square 0.9932 vs. 0.9263).

Table 1 summarizes the kinetic study of glyphosate removal by star-shaped block copolymers and activated carbon under first order reaction simulation and second order reaction simulation. The results clearly show that the glyphosate adsorption by star-shaped block copolymers and activated carbon both best fit a second order reaction.

Under second order simulation, glyphosate removal by the star polymer has double the reaction rate constant ($k_2$), which means that the star polymer can remove glyphosate from water much faster than activated carbon under the same conditions. Moreover, the star-shaped block copolymer shows an adsorption capacity ($q_e$) three times that of activated carbon, and the results are quite consistent with the experimental data shown earlier, such as $q_e$ test (MASN) =9.6 mg/g and $q_e$ second-order (MASN)=9.63 mg/g, and $q_e$ test (AC)=3.2 mg/g and $q_e$ second-order (AC)=3.18 mg/g.

TABLE 1

| Adsorbent | $C_0$ (ppm) | $q_e$ test (mg/g) | First order | | | Second order | | |
|---|---|---|---|---|---|---|---|---|
| | | | $k_1$ (min$^{-1}$) | $q_e$ (mg/g) | $R^2$ | $k_2$ (g/mg/min) | $q_e$ (mg/g) | $R^2$ |
| Activated Carbon (AC) | 5 | 3.2 | 0.015 | 1.04 | 0.9263 | 0.042 | 3.18 | 0.9932 |
| Star Polymer (SP) | 5 | 9.6 | 0.130 | 1.50 | 0.9437 | 0.086 | 9.63 | 0.9994 |

As noted above, the second order reaction rate mainly depends on the concentration of two reactants and the reaction rate (k). Since one reactant, glyphosate, has an ultra-low concentration at the ppm~ppb level, normal adsorbents have difficulty efficiently removing glyphosate. The amine-functionalized star-shaped block copolymer has a highly positive charge and a large surface area, which provides highly effective glyphosate removal from aqueous solutions.

Various embodiments of the invention have been described. These and other embodiments are within the scope of the following claims.

The invention claimed is:

1. A method comprising removing glyphosate from a solution by contacting the solution with polymeric particles having the following chemical structure:

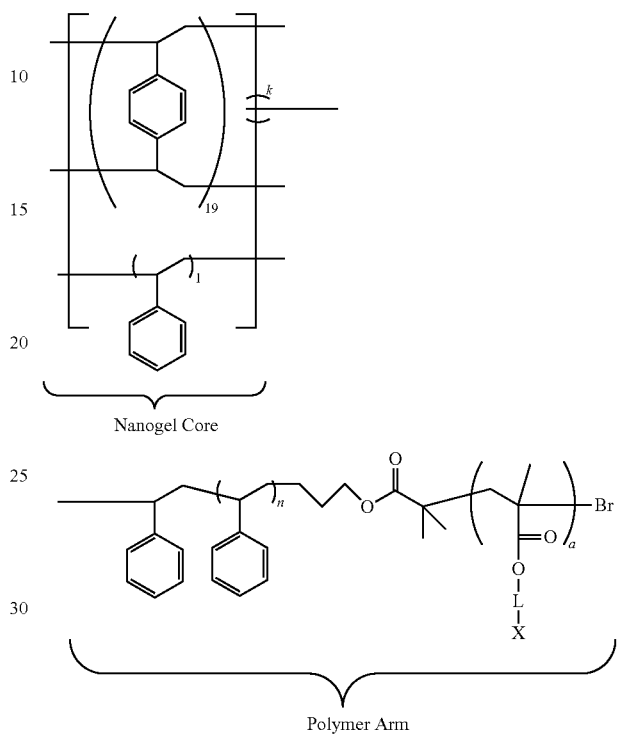

wherein the linking group (L) is selected from the group consisting of alkyl, aryl, alkenyl, and combinations thereof; X is selected from the group consisting of positively charged ammonium moieties and their precursors; k is 6 or more, n is 1 or more, and a is 2 or more.

2. The method of claim 1, wherein the solution comprises greater than 0 and less than about 5 ppm glyphosate, and wherein the polymeric particles remove at least about 94% of the glyphosate from the solution.

3. The method of claim 2, wherein the solution comprises less than about 2 ppm glyphosate.

4. The method of claim 3, wherein the solution comprises less than about 500 ppb glyphosate.

5. The method of claim 1, wherein the particles has the following chemical structure:

SP-1

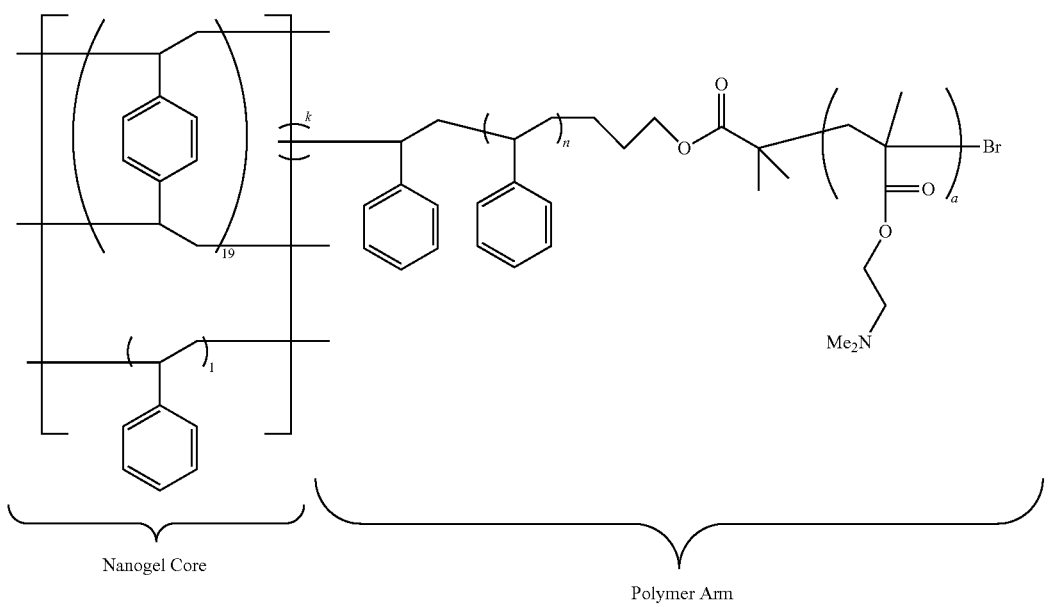

Nanogel Core | Polymer Arm wherein a is about 33, n is about 32, k is about 35, and Me = $CH_3$.

6. The method of claim 1, wherein the solution comprises water.

7. A method for removing glyphosate from an aqueous solution, comprising:
(a) adding an amine-functionalized polymeric particles into the aqueous solution containing glyphosate, wherein the polymeric particles has the following chemical structure:

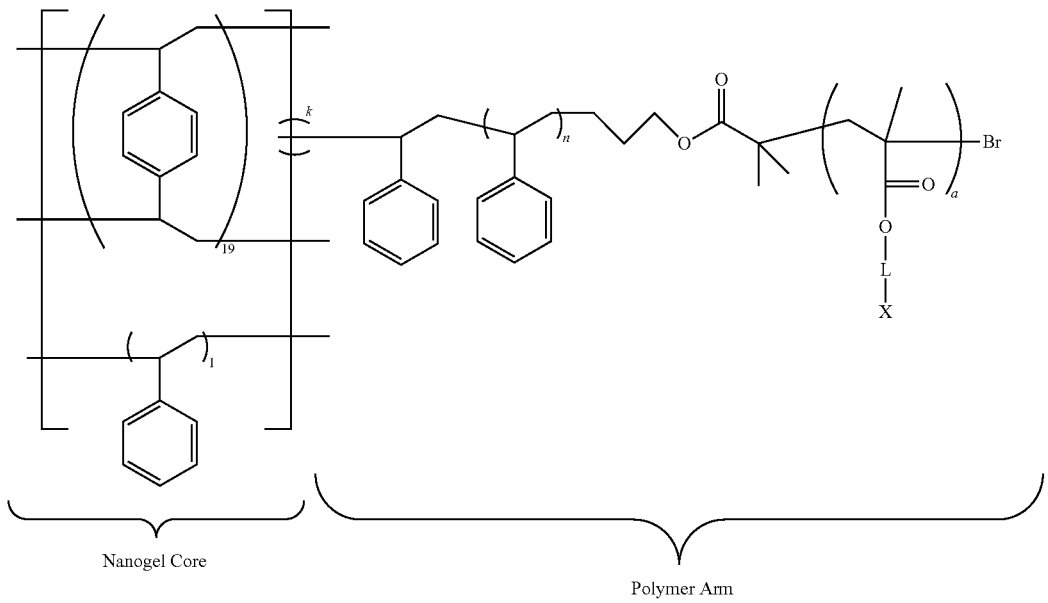

Nanogel Core | Polymer Arm wherein the linking group (L) is selected from the group consisting of alkyl, aryl, alkenyl, and combinations thereof; X is selected from the group consisting of positively charged ammonium moieties and their precursors; k is 6 or more, n is 1 or more, and a is 2 or more; and (b) filtering to remove from the aqueous solution a complex comprising the amine-functionalized polymeric particles having glyphosate adsorbed thereon, and residual amine-functionalized particles.

8. The method of claim 7, comprising stirring the aqueous solution following step (a).

9. The method of claim 8, wherein the aqueous solution is stirred for about 1 minute to about 1 hour.

10. The method of claim 7, wherein the concentration of glyphosate in the aqueous solution is greater than 0 and less than about 5 parts per billion (ppb) to 1000 parts per million (ppm), and wherein the polymeric particles remove at least about 94% of the glyphosate from the solution.

11. The method of claim 7, wherein the amine-functionalized polymeric particles have a particle size of about 10 nm to about 500 nm and a zeta potential of about 5 mV to about 50 mV.

12. The method of claim 7, wherein the filtering comprises at least one of sand filtration, microfiltration, and ultrafiltration.

13. A system, comprising:
a filtration column comprising a packing, the packing comprising polymeric particles with the following chemical structure:

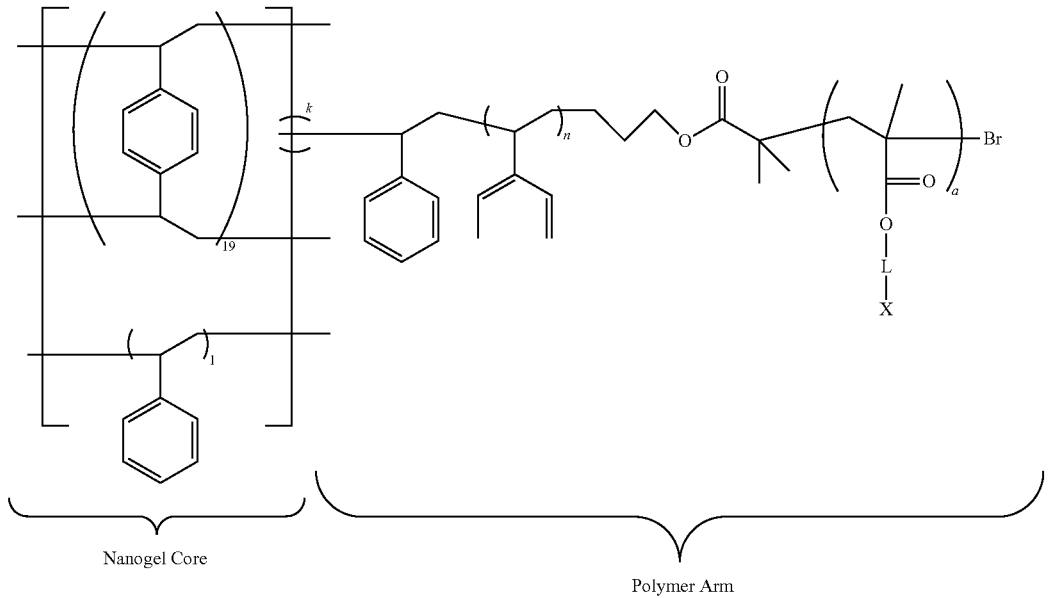

wherein the linking group (L) is selected from the group consisting of alkyl, aryl, alkenyl and combinations thereof; X is selected from the group consisting of positively charged ammonium moieties and their precursors; k is 6 or more, n is 1 or more, and a is 2 or more; and
a source providing an aqueous solution to the filtration column, wherein the aqueous solution contacts the packing, and wherein the aqueous solution comprises greater than zero and less than about 5 ppm glyphosate.

14. A system, comprising:
a filter comprising polymeric particles with the following chemical structure:

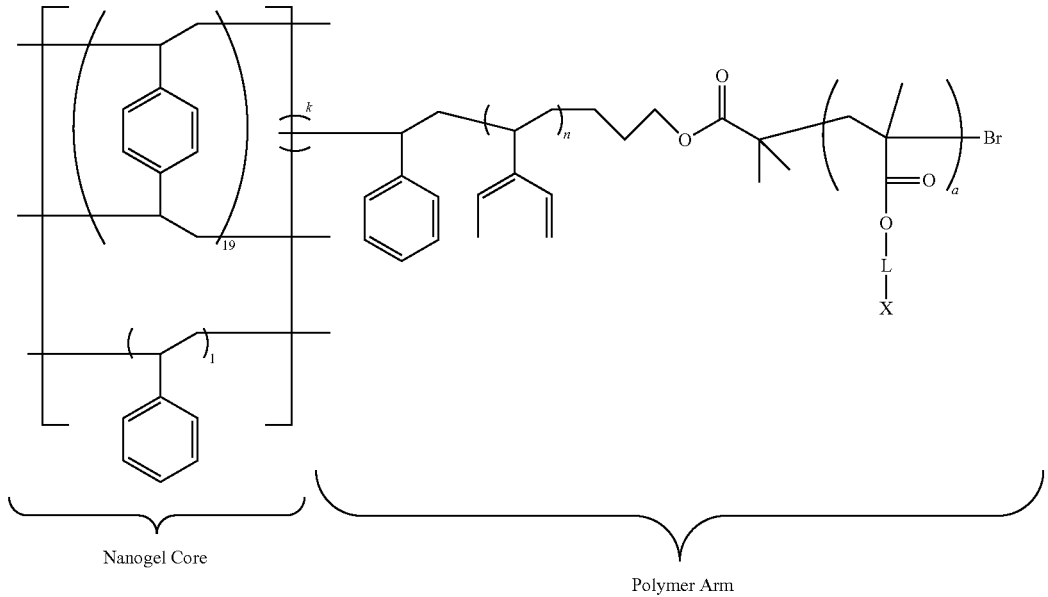

wherein the linking group (L) is selected from the group consisting of alkyl, aryl, alkenyl and combinations thereof; X is selected from the group consisting of positively charged ammonium moieties and their precursors; k is 6 or more, n is 1 or more, and a is 2 or more; and a source providing an aqueous solution to the filter, wherein the aqueous solution contacts the filter, and wherein the aqueous solution comprises greater than zero and less than about 5 ppm glyphosate.

\* \* \* \* \*